(12) United States Patent
Salmon

(10) Patent No.: US 12,145,633 B2
(45) Date of Patent: Nov. 19, 2024

(54) MULTIFUNCTIONAL TRACK SYSTEM WITH INDEPENDENTLY MOVABLE VEHICLES

(71) Applicant: Carl Anthony Salmon, Brooklyn, NY (US)

(72) Inventor: Carl Anthony Salmon, Brooklyn, NY (US)

(*) Notice: Subject to any disclaimer, the term of this patent is extended or adjusted under 35 U.S.C. 154(b) by 1030 days.

(21) Appl. No.: 16/966,755

(22) PCT Filed: Feb. 1, 2019

(86) PCT No.: PCT/US2019/016249
§ 371 (c)(1),
(2) Date: Jul. 31, 2020

(87) PCT Pub. No.: WO2019/152778
PCT Pub. Date: Aug. 8, 2019

(65) Prior Publication Data
US 2021/0039684 A1   Feb. 11, 2021

Related U.S. Application Data

(60) Provisional application No. 62/709,784, filed on Feb. 1, 2018.

(51) Int. Cl.
*B61B 3/02* (2006.01)
*B25J 9/00* (2006.01)
(Continued)

(52) U.S. Cl.
CPC .............. *B61B 3/02* (2013.01); *B25J 9/0009* (2013.01); *B61B 3/00* (2013.01); *B61B 5/00* (2013.01);
(Continued)

(58) Field of Classification Search
CPC .. B61B 3/02; B61B 13/00; B61B 5/02; B61B 3/00; B61B 5/00; B61B 15/00; E01B 25/22; E01B 25/24; E01B 25/26; B61K 13/00; B61L 15/0018; B25J 9/0009; G01N 33/0009
(Continued)

(56) References Cited

U.S. PATENT DOCUMENTS

D191,601 S * 10/1961 Scott ............................... 104/94
3,086,478 A *  4/1963 Schreyer ................. E01B 25/24
                                                        105/155
(Continued)

FOREIGN PATENT DOCUMENTS

WO    WO-2013070799 A1 *  5/2013  ............... B61B 1/00

*Primary Examiner* — S. Joseph Morano
*Assistant Examiner* — James William Jones
(74) *Attorney, Agent, or Firm* — Andrew Berks

(57) ABSTRACT

A multifunctional track system with two or more independently movable trolleys which can run along the track system and are adapted to receive multiple interchangeable components for data collection, navigation, and cargo transportation is disclosed. The trolleys and the track system communicate data to a central station, which monitors and sends instructions to the trolleys. The system can have horizontal, vertical or angular segments and the trolleys are enabled to move along all segments and switch between tracks. Various operational units in the trolleys are possible in the same system.

18 Claims, 6 Drawing Sheets

(51) Int. Cl.
  *B61B 3/00* (2006.01)
  *B61B 5/00* (2006.01)
  *B61B 5/02* (2006.01)
  *B61B 13/00* (2006.01)
  *B61B 15/00* (2006.01)
  *B61K 13/00* (2006.01)
  *B61L 15/00* (2006.01)
  *E01B 25/22* (2006.01)
  *G01N 33/00* (2006.01)
  *E01B 25/24* (2006.01)
  *E01B 25/26* (2006.01)

(52) U.S. Cl.
  CPC ............. *B61B 5/02* (2013.01); *B61B 13/00* (2013.01); *B61B 15/00* (2013.01); *B61K 13/00* (2013.01); *B61L 15/0018* (2013.01); *E01B 25/22* (2013.01); *G01N 33/0009* (2013.01); *E01B 25/24* (2013.01); *E01B 25/26* (2013.01)

(58) Field of Classification Search
  USPC .............................................. 104/89, 91, 94
  See application file for complete search history.

(56) References Cited

U.S. PATENT DOCUMENTS

| | | | |
|---|---|---|---|
| 3,861,315 A * | 1/1975 | Rypinski | B61B 15/00 104/246 |
| 3,919,946 A * | 11/1975 | Laurent | E01B 25/24 104/94 |
| 3,922,970 A * | 12/1975 | Glastra | B61L 23/005 104/111 |
| 3,965,823 A * | 6/1976 | Bardot | E01B 25/24 104/106 |
| 3,987,877 A * | 10/1976 | Bulanchuk | H02G 5/04 191/35 |
| 4,015,537 A * | 4/1977 | Graef | B61C 13/04 238/148 |
| 4,203,369 A | 5/1980 | Perrot | |
| 4,214,535 A * | 7/1980 | Gerhard | E01B 25/26 104/130.07 |
| 4,229,857 A * | 10/1980 | Toder | A47H 15/02 16/98 |
| 4,314,512 A * | 2/1982 | Gerhard | B61B 12/04 104/94 |
| 4,393,786 A * | 7/1983 | Dull | E01B 25/26 191/38 |
| 4,464,998 A * | 8/1984 | Wakabayashi | B61B 10/022 198/803.11 |
| 4,614,158 A * | 9/1986 | Helde | B61B 10/025 104/91 |
| 4,768,442 A * | 9/1988 | Miller | E01B 25/22 104/106 |
| 5,016,541 A * | 5/1991 | Feaster, Jr. | A01G 9/143 104/96 |
| 5,085,150 A * | 2/1992 | Moore | B60B 33/0015 295/36.1 |
| 5,445,080 A * | 8/1995 | Austin | B61B 13/04 105/241.1 |
| 5,592,883 A * | 1/1997 | Andress, III | B61B 3/02 105/154 |
| 5,598,785 A * | 2/1997 | Zaguroli, Jr. | E01B 25/24 104/111 |
| 6,269,944 B1 * | 8/2001 | Taylor | B66C 6/00 212/177 |
| 6,321,657 B1 | 11/2001 | Owen | |
| 6,378,440 B1 * | 4/2002 | Rhodes | B61B 10/02 104/93 |
| 7,185,589 B2 * | 3/2007 | Owens | E05D 15/0608 105/148 |
| 7,856,930 B2 * | 12/2010 | Zaguroli, Jr. | B66C 9/14 105/29.1 |
| 8,286,559 B2 * | 10/2012 | Robinson | B64D 25/06 105/155 |
| 8,458,827 B2 * | 6/2013 | Darrow | E01B 25/22 5/85.1 |
| 8,561,787 B2 * | 10/2013 | Wend | B65G 19/025 104/93 |
| 2004/0107862 A1 * | 6/2004 | Suh | B61B 3/02 104/91 |
| 2005/0098059 A1 * | 5/2005 | Wallner | B66C 11/06 104/89 |
| 2007/0039512 A1 * | 2/2007 | Ksyk | E05D 15/0608 104/89 |
| 2007/0051856 A1 | 3/2007 | Rossmann et al. | |
| 2008/0022881 A1 * | 1/2008 | Takasu | E01B 25/22 104/89 |
| 2010/0288155 A1 * | 11/2010 | Chepurny | A61G 7/1042 104/89 |
| 2013/0118371 A1 | 5/2013 | Wheeler | |
| 2013/0167750 A1 * | 7/2013 | Spies | B66C 7/08 104/93 |
| 2013/0213257 A1 * | 8/2013 | Yamamoto | H01L 21/6773 105/150 |
| 2014/0047995 A1 * | 2/2014 | Kobayashi | B61B 3/00 104/89 |
| 2014/0090575 A1 * | 4/2014 | Nagamine | E01B 25/00 104/91 |
| 2019/0049099 A1 * | 2/2019 | Baker | F21V 21/15 |

* cited by examiner

MULTIFUNCTIONAL TRACK SYSTEM WITH INDEPENDENTLY MOVABLE VEHICLES

CROSS REFERENCE TO RELATED CASE

This application is the U.S. National Stage of PCT application No. PCT/US19/16249, filed Feb. 1, 2019, which claims priority to U.S. Provisional Patent Application No. 62/709,784, filed on Feb. 1, 2018.

FIELD OF THE INVENTION

The invention relates in general to a multifunctional track system with one or more independently movable trolleys, which can move independently on the track system and are adapted to receive multiple interchangeable components for data collection, navigation and cargo transportation. The trolleys and the track system communicate data to a central station, which monitors and sends instructions to the cars.

BACKGROUND

Independently moving vehicles on a track system is very desirable in many applications. A very obvious example are public transportation rail systems, which typically have at least a double track in most locations and crossover sections where vehicles (trains) can move from one track to another. Moreover, on a public transportation rail system the track is limited scope, meaning that each rail line has two ends, and vehicles move independently of each other.

Track systems have many applications besides conventional railroads, including lightweight applications. For example, U.S. Pat. No. 6,614,468 discloses a monitoring system on a rail. U.S. Pat. No. 7,739,959 discloses a rail system for longwall mining operations. U.S. Pat. No. 6,679,181 discloses dual mode rail transportation system. In U.S. Pat. No. 7,761,890, a sensor was mounted on a trolley that moved on a monorail. In US Publication US2009/0174796, a surveillance device is mounted on a rail and moves on the rail.

None of the above references however provides for a plurality of vehicles that can move independently on a rail system and provide a plurality of functionality and track orientation, as provided in this invention. The inventive devices provide for a means for inspections, monitoring, and transport applications with improved flexibility over the prior art, and as an alternative in many applications to drones (unmanned aerial vehicles) or other aircraft. Aircraft may not be desirable in many applications. Moreover, the inventive devices can include solar panels to generate power, to allow them to be self-sufficient and/or generate excess power for other applications.

SUMMARY OF THE INVENTION

This invention provides for a plurality of independently moveable vehicles on a track system.

In an embodiment, a multifunctional track system with a plurality of independently moveable trolleys (vehicles or cars) thereon is provided, having a track system comprising one or more main channels with a longitudinal axis, where each main channel has a rectangular, square, or semicircular cross section comprising a dorsal wall, a ventral wall, and two side walls; and wherein the ventral wall is divided by a longitudinal groove therethrough; and wherein a guide channel is positioned longitudinally along the interior surface of the dorsal wall of each main channel, and wherein the main channels have one or more crossover sections.

The multifunctional track system may further include two or more independently movable trolleys that move in either direction on the track system, wherein each trolley comprises a drive unit positioned within a main channel and a drive console exterior to the main channel that travels along the exterior ventral surface, and wherein the drive unit and drive console are connected with a neck positioned within the groove; and wherein an operating section is connected to the drive console, wherein a sensory or operational device is integral with the operating section.

The multifunctional track system may further include a drive unit having at least four wheels and a support member with a contact member extending into the guide channel, and wherein at least one of the wheels is a drive wheel with motive power to move the trolley in either direction in the track system, wherein the cars can change channels at a crossover section, wherein a means is provided to deliver electric power to each trolley, wherein each trolley is adapted to receive and transmit data pertaining to the position of the trolley, instructions on the movement of the trolley within the track system, and control or reporting data for the sensory device or operational device in the operating section, wherein the track system has one or more data control stations, and wherein each trolley and the track system can send and receive data to and from a data control station.

DETAILED DESCRIPTION

A system is disclosed comprising a track system, where two or more trolleys (cars or vehicles) independently move on the track system, and a central station with which the trolleys and the track system are in continuous communication. Two or more movable trolleys can move independently in either direction on the track system.

Figures 1, 2, 3:
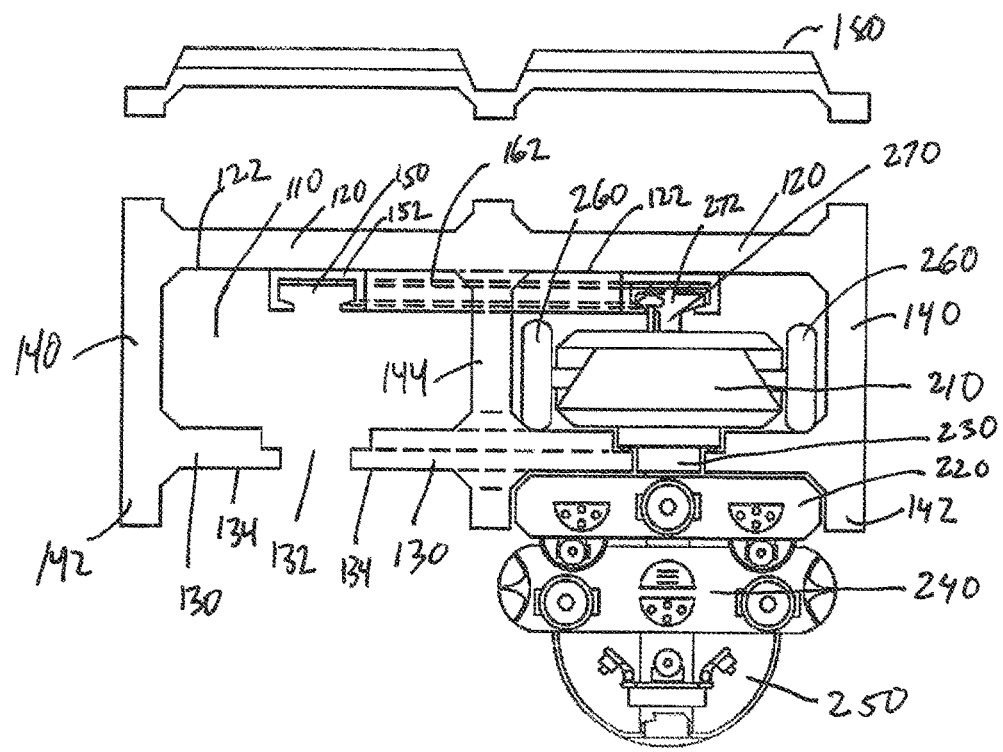
FIG. 1 is a cross-section view of a trolley according to this invention in operation on a track.
FIG. 2 is an alternative cross-section view of a trolley according to this invention with wheels in a diagonal orientation.
FIG. 3 is an alternative cross-section view of a trolley according to this invention with wheels in a perpendicular orientation.

In an embodiment illustrated in the drawings, a trolley 200 is shown in operation on a track system 100. Each track 100 has one or more main channels 110 with a longitudinal axis 112, where each main channel 110 has a rectangular, square, or semicircular cross section (if sliced on a latitudinal axis 114). The channels are defined by a dorsal wall 120, a ventral wall 130, and two side walls 140. The ventral wall 130 may be divided by a longitudinal groove 132 therethrough. A guide channel 150 may be positioned longitudinally along the interior surface 122 of the dorsal wall 120 of each main channel 110. The main channels may have one or more crossover sections 160 through which the trolley 200 can change lanes and/or tracks 100. In FIGS. 1-3, a crossover guideway is shown as 162. In an embodiment of the present invention, the tracks 100 have two or more channels 110 positioned side by side. In an embodiment each section of track 100 comprises a side-by-side pair of channels 110, with a common wall 144 in the center.

Each trolley 200 may have a drive unit 210 positioned within a main channel 110 and an operating section 240 exterior to the main channel 110, connected with a neck 230 positioned within the groove 132 in the ventral wall 130 of the main channel 110. An optional drive console 220 exterior to the main channel 110 that travels along the exterior surface 134 of the ventral wall 130 can be mounted between the neck 230 and the operating section 240. The operating section 240 may be connected to the drive console 220 if a drive console is present. The operating section may include one or more sensory and/or operational devices 250. The drive console, if present, may be nested in a channel defined by the exterior surface of the ventral wall 134, and overlay edges 142. A drive console 220 may provide, for example, a mounting means for a variety of operating sections and operating devices.

In an embodiment of the present invention, each trolley 200 is equipped with one or more independently different sensory or operational devices, which can be removably mounted on an operational unit/section 240, the console 220 or the neck 230. In an embodiment, different trolleys 200 may have different sensory or operational devices, and this plurality of devices operates on the same system simultaneously. For example, a particular trolley may have an operational device comprising a video camera (illustrated in FIG. 1, 250), and a second trolley on the same track system may have a temperature sensor as an operational device. In an embodiment, the trolleys can move independently. So for example, a temperature sensor operational unit may be stationed at a specific location, and a video camera operational unit may move anywhere else on the track. Because of the crossover sections, the trolley with the video camera may move around the trolley with the temperature sensor.

The operational unit/section 240 of each trolley 200 may host one or more sensory devices such as a video camera or other imaging device, a microphone, a proximity or motion detector, an environmental sensor, such as from a thermometer, a humidistat, an air pressure sensor, a chemical sensor, for instance, a carbon monoxide detector, a carbon dioxide detector, a detector for another specific airborne substance, an infrared detector, and an air sampling device or a combination thereof.

The operational unit/section 240 of each trolley 200 can be equipped with a mechanical device such as a robotic arm, an environmental sampling device, and a cargo carrying device. In an embodiment, this invention may be of a size and power to permit it to carry heavy loads, such as large boxed items or mining material.

In an embodiment, power is provided to each trolley from conductors 152 in the guide channel 150. However, other embodiments of transmitting electrical power to the trolleys are possible, such as guide rails or conducting rails in other locations. In another embodiment, a trolley may be equipped with batteries and be designed to operate for a period of time with no external power connection.

An operating section 240 can have the ability for angular movement, rotation, vertical and or horizontal movement, which would allow the operational devices, sensory and mechanical, to focus, point or reach in different directions at the same time.

The sensory or operational devices that a trolley can carry can be adapted and capable of supporting various weights, from less than 1 kg, less than 10 kg or less than 100 kg.

In an embodiment of this invention, the trolleys 200 and the track system 100 can be designed and manufactured for heavy industrial applications and be adapted and capable of carrying devices or heavy cargo weighting more than 100 kg.

The inventive multifunctional track system can be deployed in various embodiments in either indoor or outdoor locations. Depending on the application, the track system may be less than 100 m long or can be longer than 100 m, 1 km or in some embodiments be longer than 10 km. For example, the inventive multifunctional track system can be used to monitor security and environmental parameters on the perimeter of a manufacturing plant. In another example, the inventive multifunctional track system can be used to monitor environmental parameters in an interior location, such as inside a manufacturing plant or a mall.

The trolleys 200 may be adopted for indoor or outdoor use and may be designed to be weather resistant and employ hazardous weather resistant materials. In an embodiment, the trolleys may employ chemically resistant materials, allowing the trolley and operational devices to operate in hazardous environments or under different weather conditions, including harsh weather conditions such as high winds or rain.

In an embodiment of the present invention each trolley 200 has two or more wheels such as wheels 260, and preferably four or more wheels. In an embodiment, at least one of the wheels is a drive wheel that provides motive power to move the trolley in either direction in the track system. The drive wheel may be powered by an electric motor in the axle, or by a gearing mechanism in the drive unit 210.

Figure 13:
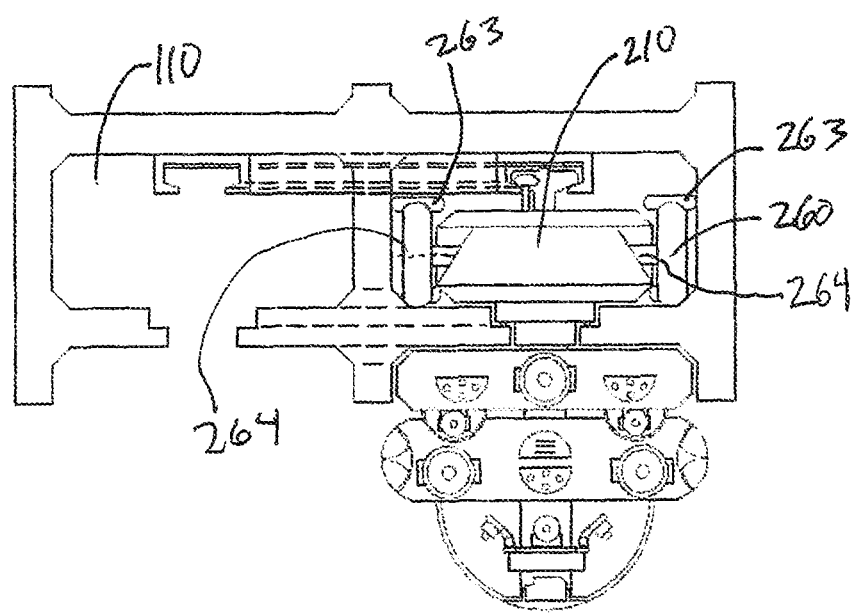
FIG. 13 is an alternative cross-section view of a trolley according to this invention with wheels in contact with the interior ventral surface and the side walls.

As depicted in FIGS. 2-3 the wheels can be installed in alternative orientations. In FIG. 2, the wheels 261 are installed in diagonal orientation with wheel axes 264 at an approximately 45° or 135° angle with respect to wall 130, and in FIG. 3 in a horizontal orientation with the wheel axis 262 perpendicular relative to the surface 136 of the ventral wall 130. In FIG. 13, there are two sets of wheels with axles in opposing directions, for example, there is a wheel set oriented as in 260, which is principally in contact with the ventral interior surface 136, and a second set of wheels 263 that are in contact with side walls 140.

Figure 4:
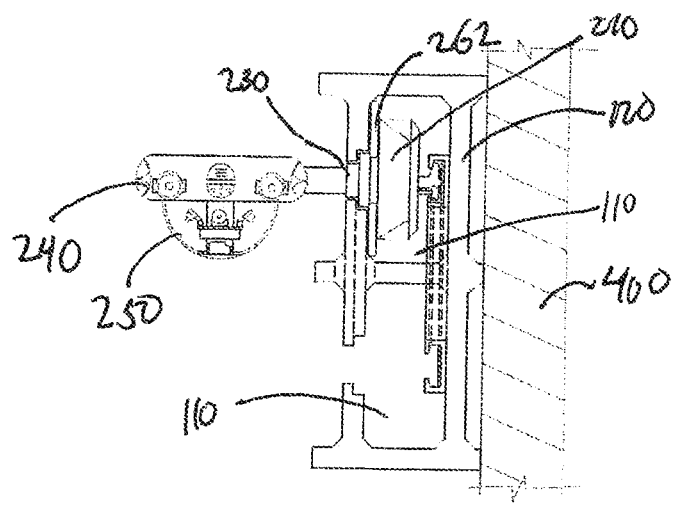
FIG. 4 is an alternative cross-section view of a trolley according to this invention with wheels in a perpendicular orientation, in which the track is in a vertical orientation running parallel to the ground, and an operational unit oriented appropriately for the application.

In FIG. 4 an embodiment of the present invention is shown with the track's latitudinal axis 114 at a vertical orientation with respect to the ground (not shown) and in a configuration where the operating section 240 is mounted on the neck 230 perpendicularly to the exterior surface 134 of the ventral wall 130. A building wall 400 is depicted in FIG.

4, showing the dorsal wall 120 affixed to the building, with each channel 110 in a dual track in an over/under configuration.

In an embodiment of the present invention, the trolleys 200 move along the main channels 110, powered by electric power or propelled by magnetic levitation.

Figure 5:
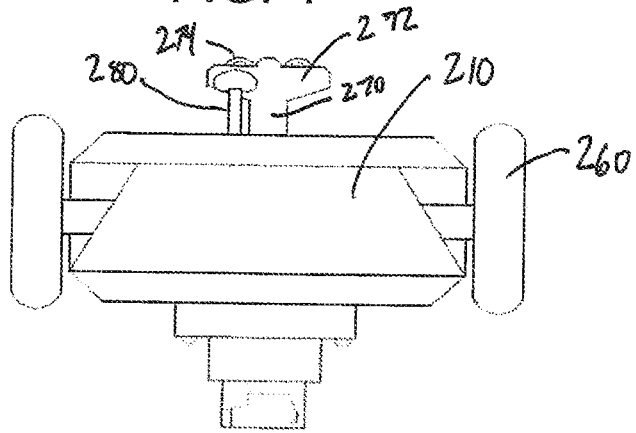
FIG. 5 is partial elevation view of the drive unit of an inventive trolley.

In an embodiment, each drive unit 210 has a support member 270 with a contact member 272, which extends into the guide channel 150 to allow the electrical contact 274 positioned on the contact member to contact the electrical conductors positioned 152 along the guide channel 150. FIG. 5 is a partial elevation view of an embodiment of the inventive trolley 200 with a close-up view of the support member 270 and the contact member 272. In an embodiment, some of the conductors 152 may transmit electric power, and others may be data channels.

Figure 6:
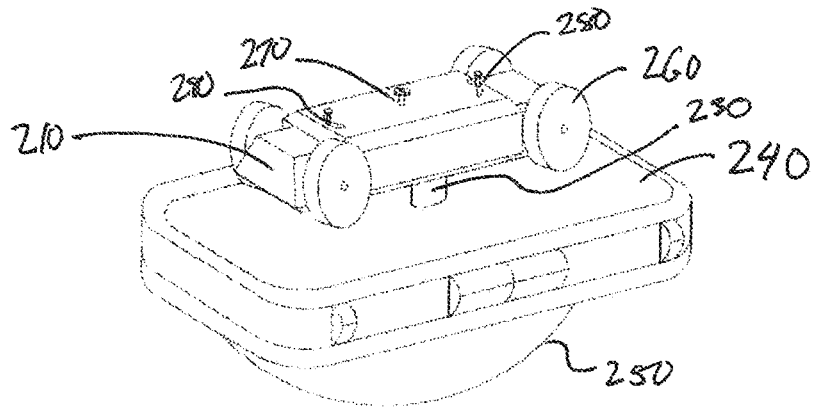
FIG. 6 is a perspective view of an inventive trolley without the track.

FIG. 6 is a perspective view of an inventive trolley without the track. In the embodiment illustrated, two or more steering guides 280 are positioned on the drive unit 210 allow the trolley to turn and direct the movement of the trolley 200 in the crossover sections. In the embodiment depicted in FIG. 6, there is no drive console 220. Rather, as shown in FIG. 6, drive unit 210 is connected to operating section 240 directly through neck 230.

Figure 7:
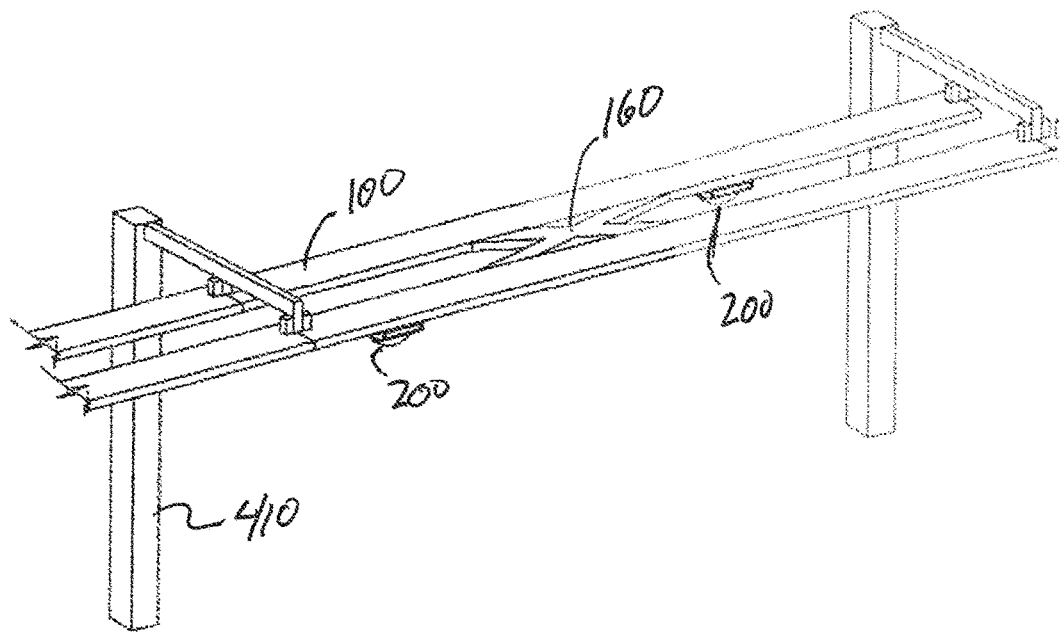
FIG. 7 shows a section of track with a crossover section. In this embodiment, the track is mounted horizontally.

FIG. 7 is an exemplary depiction of an elevated section of the multifunctional track system with the two side-by-side tracks positioned in horizontal orientation and two trolleys moving along each track and a crossover section 160, allowing the trolleys to switch tracks at the crossover section 160. FIG. 7 also depicts an embodiment showing the track supported by brackets 410. In other embodiments, the track may be affixed to a wall 400.

The multifunctional track system can be designed to follow the characteristics of the terrain and run along the walls, ceilings or floors, for instance. Bends and/or corners are provided in the tracks 100 so that the track direction in the longitudinal direction 112 can change from parallel to the ground or vertical to the ground, in either vertical orientation.

Figure 8:
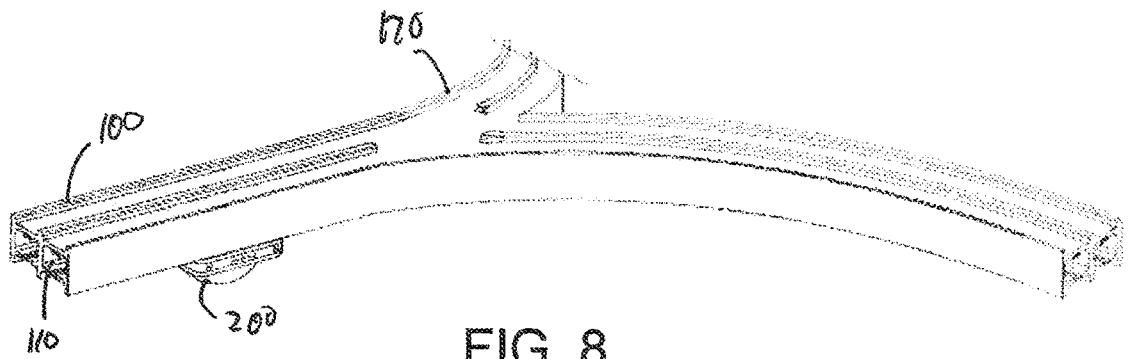
FIG. 8 shows a section of track with a corner.

The multifunctional track system 100 can have segments, where the tracks 100 bend to form a turn or "Y" as depicted by 170 in FIG. 8.

Figure 9:
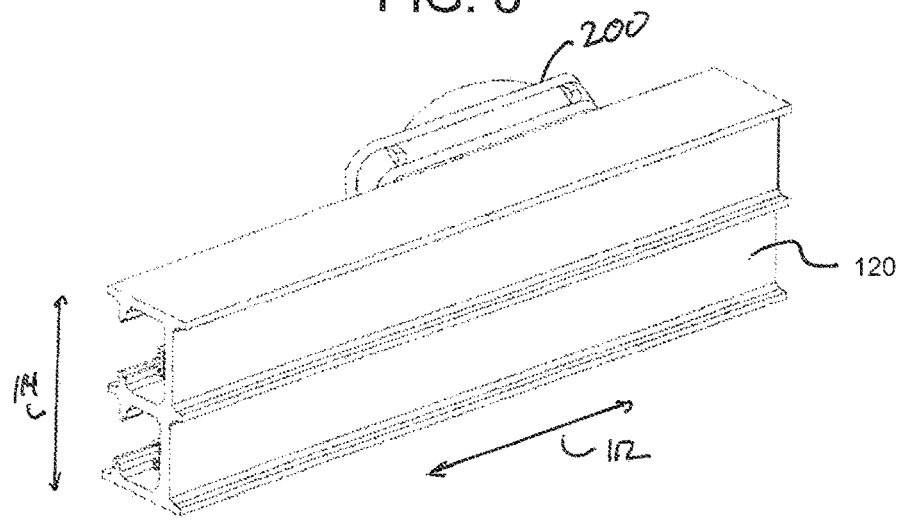
FIG. 9 shows a section of track mounted vertically where the longitudinal direction is generally parallel to the ground.

FIG. 9 is a perspective view of a segment of the track system 100 in accordance with an embodiment of the present invention. This is the same orientation as shown in FIG. 4, but with a different angle of view. In FIG. 9, the track 100 mounted vertically such that a latitudinal axis 114 of the dorsal wall 120 of the track 100 is generally perpendicular to the ground and the longitudinal direction 112 of the track 100 is generally parallel to the ground.

Figure 10:
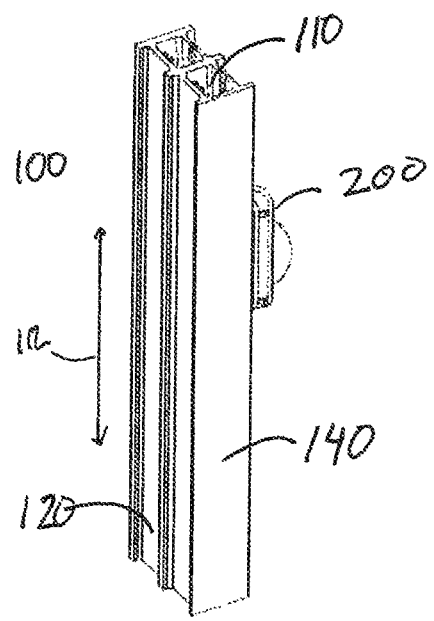
FIG. 10 shows a section of track mounted vertically where the longitudinal direction is generally perpendicular to the ground.

FIG. 10 is a perspective view of a segment of the tracks system 100 in accordance with an embodiment of the present invention or where the tracks 100 are mounted vertically such that a latitudinal axis 114 of the dorsal wall 120 of the track is generally parallel to the ground and the longitudinal axis 112 of the track 100 is generally perpendicular to the ground.

In an embodiment, each trolley 200 may be adapted to receive and transmit data pertaining to the position of the trolley, instructions on the movement of the trolley within the track system, and/or control or reporting data for the sensory device or operational device in the operating section. In an embodiment, control units 300 manage the operation data transmission of the trolleys on the tracks. In an embodiment, control unit 300 may include computer components, such as a CPU, a mother board, RAM memory, non-volatile memory, possibly a user interface, and data transmission and receiving means.

In an embodiment, the control unit 300 may have programming means, so that programmatic instructions can be provided, for example to move a trolley to a specific location on a certain day. In a programmatic embodiment, a computer program employing a computer language that the computer is adapted to read and interpret may be employed. The computer program may be stored in non-volatile memory, and computer means well known in the art may read the program, perform the programmatic tasks in the computer, and issue instructions to external devices. For example, programmatic instructions may be provided to provide basic control of the trolleys, for example to avoid collisions, or instructions to permit one trolley in motion to move to a different track to drive around another trolley in a stationary position. Programmatic instructions can employ decision making steps based on input from sensory devices, timers, or other triggers. For example, if a chemical sensor detects a certain substance, the program may have instructions to cause an alarm to be issued, or it may instruct another trolley with a different operating unit to move to another location.

In an embodiment, a plurality of control units 300 may be provided. For example, with large installations, it may be more practical to have several control units. In an embodiment, a control unit 300 may be in contact with additional fixed or mobile computers depicted as 320 and smartphone 330, that permit a human operator or other master control to program the control unit 300 or make specific requests. For example, an air-sampling sensor can be programmed to move to a certain spot at a certain time of the day. A specific request might be a command to move an imaging device to follow a moving target. In an embodiment, computers such as 320 or 330 are in a remote location from the track installation, to permit human operators to direct the operation of the trolleys on the tracks.

Figure 11:
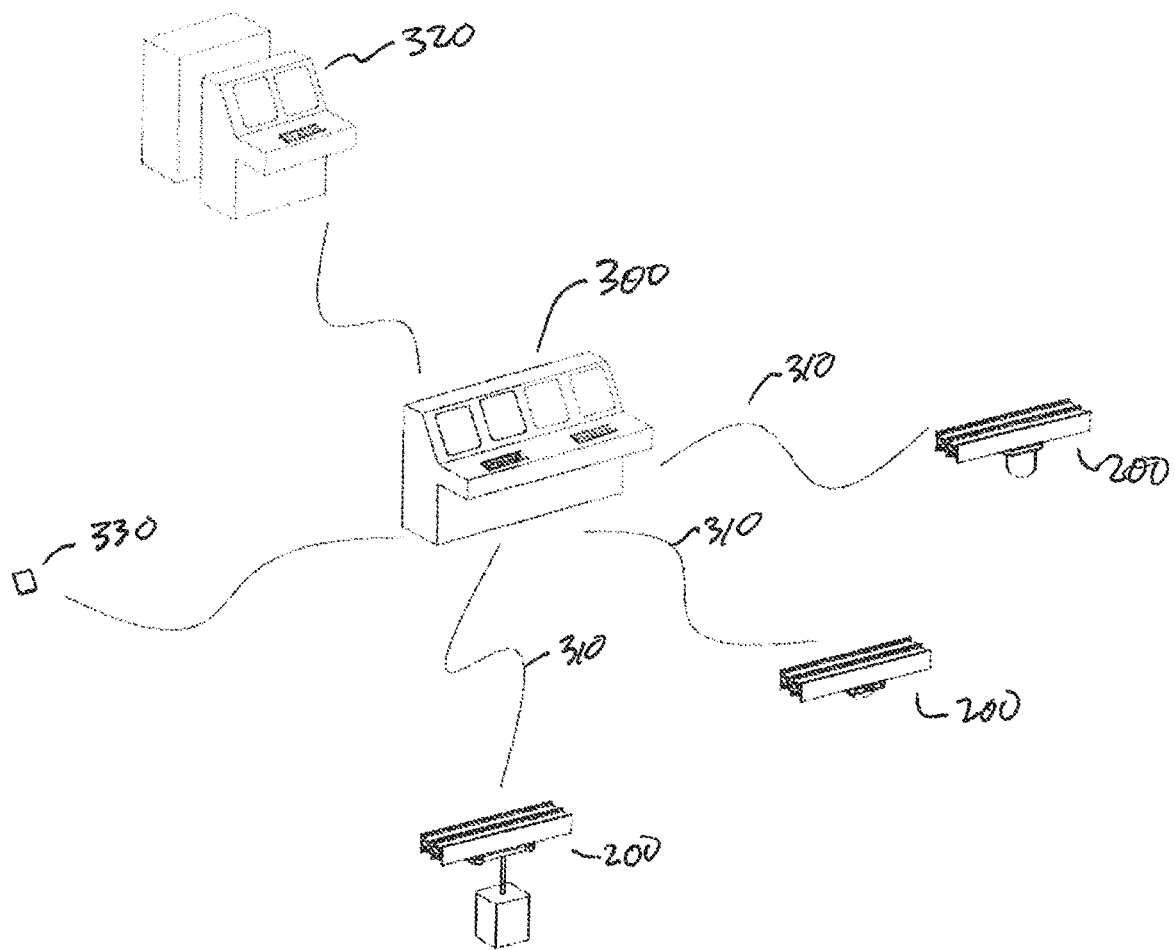
FIG. 11 shows a schematic of the data transfer in this invention.

The transmission of data is depicted by lines 310 in FIG. 11. The data transmission can be wireless, for example with WiFi, cellular data, or some other radio transmission protocol. In an embodiment, the data transmission can be hard wired through a conductor 152 in the guide channel. Regardless of the mode of data transmission, data security protocols may be employed, such as encrypted transmissions.

As shown in FIG. 11, an embodiment of the multifunctional track system has one or more data control stations 300, with which each trolley 200 and the track system communicates to send and receive data to and from the control station 300, which operation is supervised by a supervisory device 320.

In an embodiment, each trolley may also have computing power to control the operational devices on the trolley. In this embodiment, each trolley will have a computer with a CPU or microcontroller, RAM memory, non-volatile memory, and data transmission and receiving means. The trolleys in many embodiments will need computer control for operational devices, such as a video camera, an imaging device, a microphone, a proximity or motion detector, and an environmental sensor, where the environmental sensor is selected from a thermometer, a humidistat, an air pressure sensor, a chemical sensor, and an air sampling device. A chemical sensor may be selected from a carbon monoxide detector, a carbon dioxide detector, a detector for another specific airborne substance, and an infrared detector. Moreover, mechanical devices such as a robotic arm, an environmental sampling device, and a cargo carrying device may be part of the operating unit.

A computer on the trolley can be located in the drive unit 210, a console 220, or the operating section 240. In an embodiment, each of these sections may include their own computers. In an embodiment, data collected by a sensor in an operating device 250 can be stored within the trolley in non-volatile memory, for example an SD card or computer hard drive. In an embodiment, such data may be transmitted in real time to a control unit 300.

Figure 12:
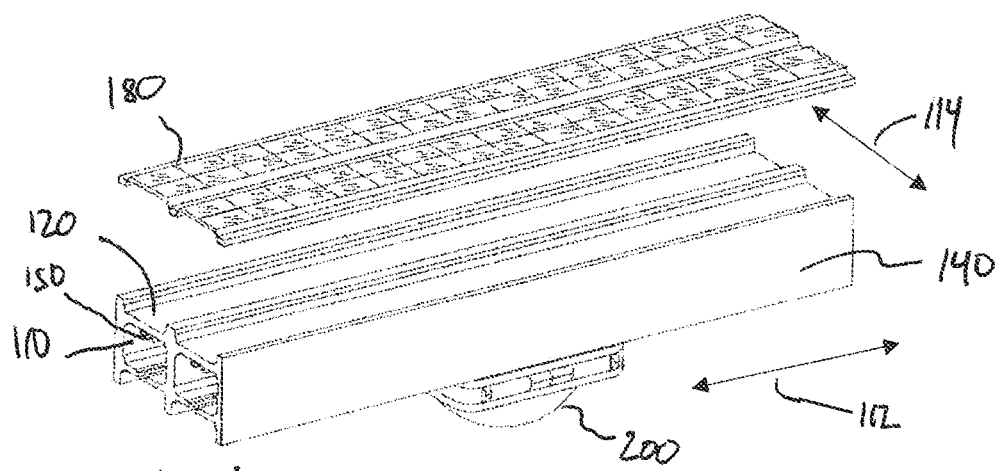
FIG. 12 is a perspective view of a section of track showing a trolley and also illustrating the longitudinal and latitudinal orientations of the track system with a solar panel to be attached to it.

In an embodiment of the multifunctional track system a solar panel may be attached to the tracks to power the system. FIG. 12 is a is a perspective view of a section of track showing a trolley 200 mounted below the tracks 100, and also illustrating the longitudinal and latitudinal orientations of the track system and a solar panel 180 to be attached on the top of the dorsal surface 120. A solar panel is also shown in FIG. 1. In an embodiment, the inventive multifunctional track system may produce excess power from the solar panels that can be supplied to other devices.

In an embodiment, a section of track may be provided that is removable or detachable to permit trolleys to be installed or removed from the inventive multifunctional track system.

LEGEND FOR THE DRAWINGS

| | |
|---|---|
| 100 | Track system |
| 110 | Main channel |
| 112 | Longitudinal axis of track |
| 114 | Latitudinal axis of track |
| 120 | Dorsal wall |
| 122 | Dorsal wall interior surface |
| 130 | Ventral wall |
| 132 | Groove in ventral wall |
| 134 | Exterior surface of ventral wall |
| 136 | Interior surface of ventral wall |
| 140 | Side walls of main channel |
| 142 | Overlay edge |
| 144 | Common side wall between two main channels. |
| 150 | Guide channel |
| 152 | Electrical conductors in guide channel |
| 160 | Crossover section in track |
| 162 | Crossover path in cross section |
| 170 | Bend or corner in track |
| 180 | Solar array |
| 200 | Trolley |
| 210 | Trolley drive unit |
| 220 | Trolley drive console |
| 230 | Neck connecting trolley drive unit and drive console |
| 240 | Operating unit/section of trolley |
| 250 | Operational device |
| 260 | Wheel on drive unit |
| 261 | Wheel in diagonal orientation |
| 262 | Wheel in perpendicular orientation |
| 263 | Wheel in contact with side walls. |
| 264 | Wheel axis |
| 270 | Trolley support member |
| 272 | Contact member |
| 274 | Electrical contact on trolley |
| 280 | Steering guide |
| 300 | Data control station |
| 310 | Data transfer to trolleys |
| 320 | Supervisory device |
| 330 | Smartphone |
| 400 | Wall supporting track |
| 410 | Brackets supporting track |

The invention claimed is:

1. A multifunctional track system with a plurality of independently movable trolleys thereon, comprising:
a track system comprising one or more main channels with a longitudinal axis, where each main channel has a rectangular or square cross section comprising a dorsal wall, a ventral wall, and two side walls; and wherein the ventral wall is divided by a longitudinal groove therethrough; and wherein a guide channel is positioned longitudinally along the interior surface of the dorsal wall of each main channel, and wherein the main channels have one or more crossover sections;
wherein two or more independently movable trolleys are provided that move in either direction on the track system, wherein each trolley comprises a drive unit positioned within a main channel, an operational unit hosting one or more sensory or mechanical devices;
wherein the drive unit has at least four wheels and a support member with a contact member extending into the guide channel, and wherein at least one of the wheels is a drive wheel that provides motive power to move the trolley in either direction in the track system;
wherein the trolleys can change channels at a crossover section;
wherein a at least two electrical conductors in the guide channel deliver electric power to each trolley;
wherein each trolley is adapted to receive and transmit data pertaining to the position of the trolley, instructions on the movement of the trolley within the track system, and control or reporting data for the sensory device or operational device in the operating section; and
wherein the track system has one or more data control stations, and wherein each trolley and the track system can send and receive data to and from a data control station.

2. The multifunctional track system of claim 1, wherein the track system comprises dual channels side-by-side.

3. The multifunctional track system of claim 1, wherein the track system is mounted horizontally such that the dorsal wall is generally parallel to the ground; or where the track system is mounted vertically such that a latitudinal axis of the dorsal wall of the track is generally perpendicular to the ground and the longitudinal direction of the track is generally parallel to the ground; or where the track system is mounted vertically such that a latitudinal axis of the dorsal wall of the track is generally parallel to the ground and the longitudinal direction of the track is generally perpendicular to the ground; and wherein bends or corners are provided in the track so that the track direction in the longitudinal direction can change from parallel to the ground or vertical to the ground, in either vertical orientation.

4. The multifunctional track system of claim 1, wherein the axis of the wheels of the trolley are oriented at an approximately 45-degree angle from the latitudinal axis of the drive unit.

5. The multifunctional track system of claim 1, wherein the axis of the wheels of the trolley are oriented at an approximately 90-degree angle from the latitudinal axis of the drive unit.

6. The multifunctional track system of claim 1, wherein the operational unit of each trolley contains at least one sensory device selected from a video camera, an imaging device, a microphone, a proximity or motion detector, and an environmental sensor.

7. The multifunctional track system of claim 6 wherein the environmental sensor is selected from a thermometer, a humidistat, an air pressure sensor, a chemical sensor, and an air sampling device.

8. The multifunction track system of claim 7, wherein the chemical sensor is selected from a carbon monoxide detector, a carbon dioxide detector, and an infrared detector.

9. The multifunctional track system of claim 1, wherein the operational unit of each trolley contains at least one mechanical device selected from a robotic arm, an environmental sampling device, and a cargo carrying device.

10. The multifunctional track system of claim 1, wherein the operational unit of each trolley is adapted to carry a sensory or operational device with a weight of less than 1 kg, of less than 10 kg, a weight of less than 100 kg, or a weight of greater than 100 kg.

11. The multifunctional track system of claim 1, wherein the operational unit of each trolley is adapted to carry an operational device capable of transporting heavy cargo.

12. The multifunctional track system of claim 1, further comprising solar panels to power the system.

13. The multifunctional track system of claim 1, wherein the track system is outdoors or inside a building.

14. The multifunctional track system of claim 1, wherein the track system is outdoors and has a track length of greater than 100 m.

15. The multifunctional track system of claim 1, wherein the track system is outdoors and has a track length of greater than 1 km.

16. The multifunctional track system of claim 1, wherein the track system is outdoors and has a track length of greater than 10 km.

17. The multifunctional track system of claim 1, wherein the track system has trolleys with two or more independently different sensory or operational devices.

18. The multifunctional track system of claim 1, wherein one or more of the independently movable trolley further includes a drive console exterior to the main channel that travels along the exterior ventral surface, and wherein the drive unit and drive console are connected with a neck positioned within the groove; and wherein an operating section is connected to the drive console; and wherein a sensory or mechanical device is integral with the operating section.

* * * * *